US00PP14233P29

(12) United States Plant Patent
Cesarini

(10) Patent No.: US PP14,233 P2
(45) Date of Patent: Oct. 14, 2003

(54) INKBERRY PLANT NAMED 'GOLD MINE'

(50) Latin Name: *Ilex glabra*
Varietal Denomination: 'Gold Mine'

(75) Inventor: Gabriel Cesarini, Ridgely, MD (US)

(73) Assignee: CP Delaware, Inc., Wilmington, DE (US)

( * ) Notice: Subject to any disclaimer, the term of this patent is extended or adjusted under 35 U.S.C. 154(b) by 3 days.

(21) Appl. No.: 10/265,734

(22) Filed: Oct. 8, 2002

(51) Int. Cl.[7] ..... A01H 5/00
(52) U.S. Cl. ..... Plt./247
(58) Field of Search ..... Plt./247

*Primary Examiner*—Kent Bell
(74) *Attorney, Agent, or Firm*—Burns, Doane, Swecker & Mathis, L.L.P.

(57) ABSTRACT

A new variety of *Ilex glabra* plant is provided that is well suited for growing as attractive ornamentation in the landscape. The new variety is believed to be a spontaneous mutation of the 'Shamrock' variety (non-patented in the United States) of unknown causation. The foliage of the new variety is particularly distinctive and when exposed to full sun is dark glossy green with irregular bright golden yellow variegation at the margin. The growth habit is slow to moderate and the plant assumes a smaller overall size than the 'Shamrock' variety. Dioecious female flowers are formed. Good hardiness is displayed in U.S.D.A. Hardiness Zone No. 6a.

4 Drawing Sheets

Botanical commercial classification *Ilex glabra*/Inkberry Plant.
Varietal denomination: cv. 'Gold Mine'.

SUMMARY OF THE INVENTION

The new variety of the present invention is a distinctive variegated sport of *Ilex glabra* 'Shamrock' (non-patented in the United States). Holly plants at this species sometimes are known as Inkberry.

A single plant of the new variety was discovered while growing in a block of *Ilex glabra* 'Shamrock' plants in a cultivated area of my nursery at Ridgely, N.J. The new variety is believed to be a spontaneous mutation of unknown causation. I was attracted to the new variety in view of its distinctive combination of characteristics. Had the new variety not been discovered and preserved by me it would have been lost to mankind.

It was formed that the new variety of the present invention exhibits the following combination of characteristics:

(a) when exposed to full sun the foliage is dark glossy green with irregular bright golden yellow variegation at the margin, (b) exhibits a slow to moderate growth habit, (c) forms dioecious female flowers, (d) assumes a smaller overall size than the parent 'Shamrock' variety (non-patented in the United States), and (e) displays good hardiness in U.S.D.A. Hardiness Zone No. 6a.

The new variety of the present invention can be readily distinguished from its 'Shamrock' parent in view of its smaller stature and distinctive variegated foliage. For instance, a five year-old plant of the new variety has been observed to commonly assume a height of only approximately 25 inches and a width of only approximately 18 inches. The mature height of the new variety is unknown; however, a mature height of only approximately 3 to 4 feet is anticipated in view of observations to date.

The new variety of the present invention well meets the needs of a the horticultural industry and can be grown in full sun to provide distinctive ornamentation. For instance, it can be grown as a colorful low hedge or as a specimen plant in the landscape.

The varying leaf coloration described herein is believed to be due to the chimeric nature of the leaf tissue. Layers of tissue containing varying amounts of pigments as well as different pigments are believed to overlay each other thereby creating the visual image of a patchwork of areas of subtly different colors.

The new variety of the present invention has been asexually reproduced by the use of terminal semi-hardwood cuttings taken in June and July at Ridgely, Md. and at West Grove, Pa. It has been demonstrated that the unique combination of characteristics is firmly fixed and is transmitted to successive generations following such asexual propagation. Even when cuttings are taken from less variegated branches that are grown in the shade, the offspring will continue to exhibit strong variegation when grown in full sunshine.

The new variety has been named 'Gold Mine'.

BRIEF DESCRIPTION OF THE PHOTOGRAPHS

The accompanying photographs show specimens of the new variety in color as nearly true as it is reasonably possible to make the same in color illustrations of this nature. The plants were growing outdoors on their own roots in containers in a nursery setting at West Grove, Pa. Such plants had been propagated by the use of semi-hardwood cuttings and were approximately five years of age. Dimensions in centimeters are included at the bottom of each photograph.

FIG. 1 illustrates a current season shoot that had been exposed to full sun. Some leaves had been removed so as to better reveal the stem. The attractive glossy bright golden yellow variegation at the margin is illustrated.

Figure 1:
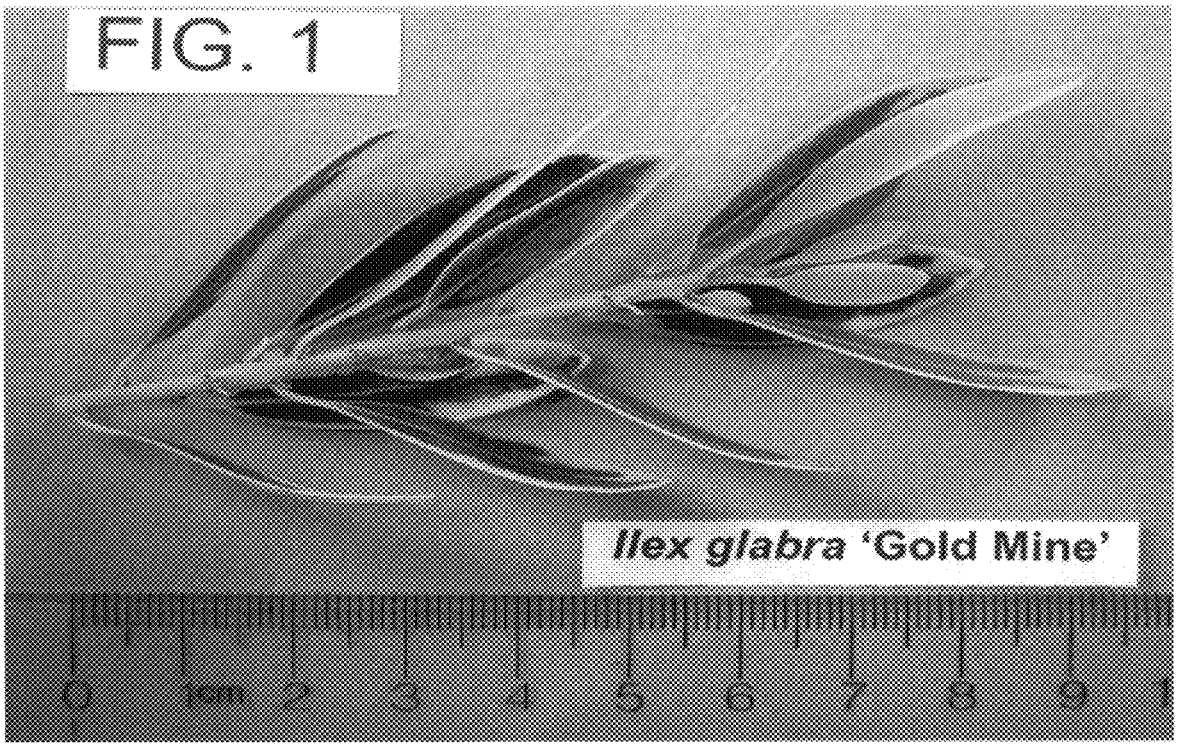
Figure 2:
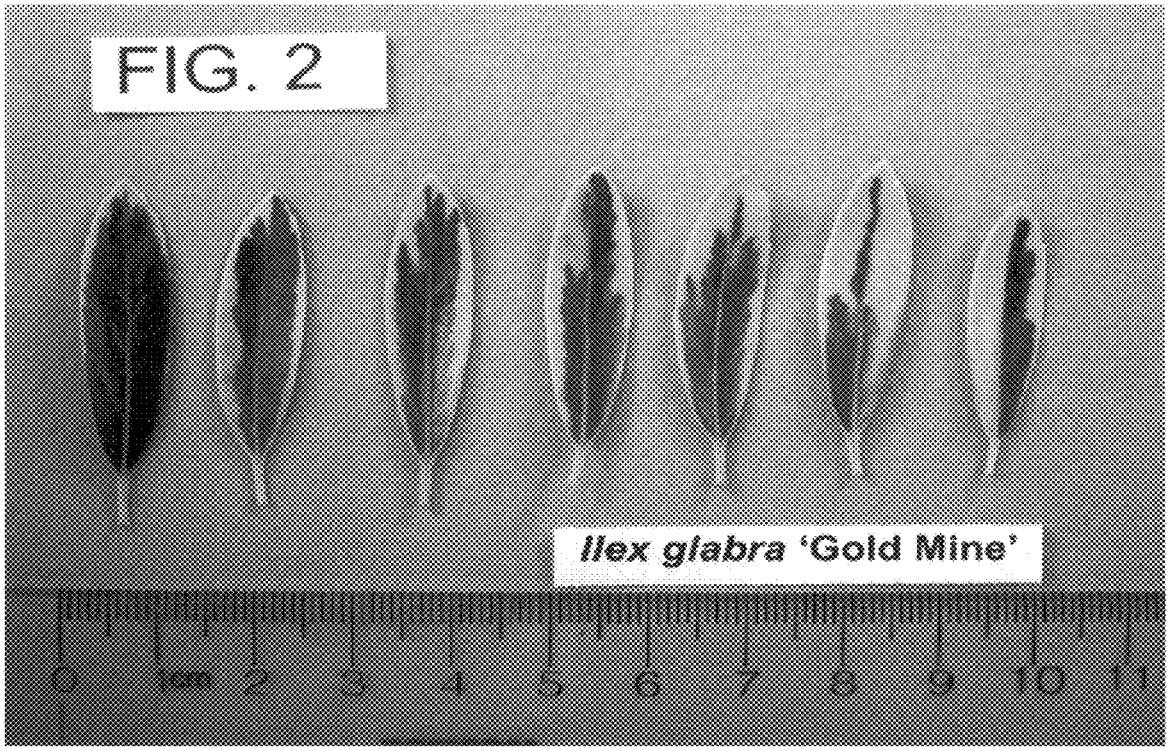
FIG. 2 illustrates the upper (ventral) surfaces of a number of representative current season mature leaves that have been exposed to the sun. The irregular nature of the bright golden yellow marginal variegation is illustrated.
Figure 3:
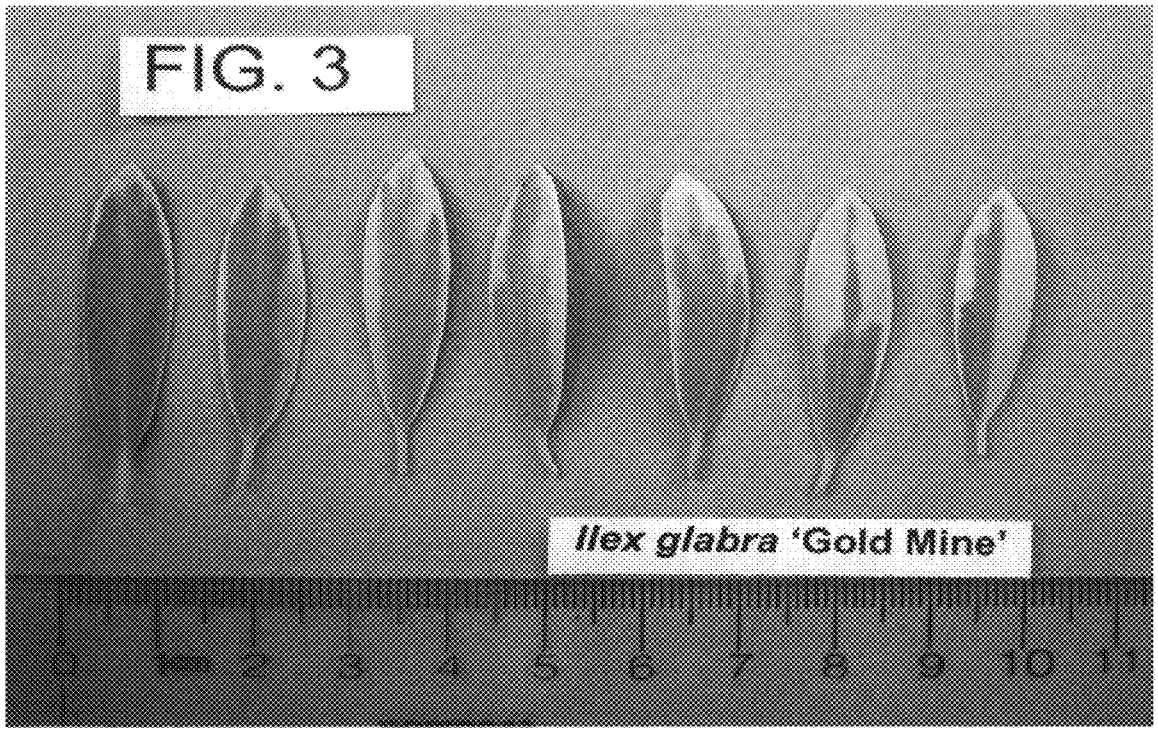
FIG. 3 illustrates the under (dorsal) surfaces of a number of representative current season mature leaves that have had exposure to the sun.
Figure 4:
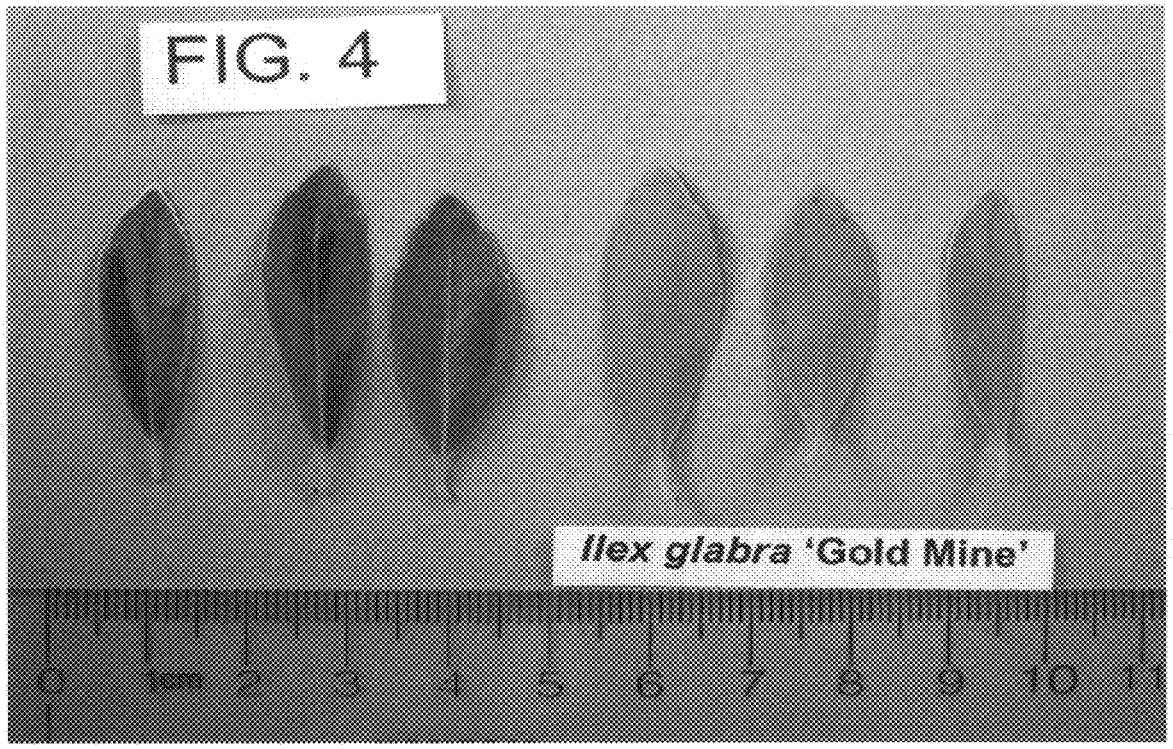

FIG. 4 illustrates representative current season mature leaves from the more shaded interior of the plant. The upper (ventral) surfaces are shown for the three leaves on the left and the under (dorsal) surfaces are shown for the three leaves on the right. It will be noted that marginal variegation is slight or nonexistent on leaves from more shaded areas of the plant.

DETAILED DESCRIPTION

The following is a detailed description of the new variety that was obtained while observing plants of approximately five years of age during the summer. Such plants had been propagated with the use of semi-hardwood cuttings and were growing in containers at West Grove, Pa. while present in a hoop house where they were fully exposed from mid-spring to mid-fall and were covered with a sheet of plastic during the winter. The plants received no supplemental heating. The chart used in the identification of color is The R.H.S. Colour Chart of The Royal Horticultural Society, London, England. Common color terms are to be accorded their customary dictionary significance.

Botanical classification: *Ilex glabra,* cv. 'Gold Mine'.

*Parent.*—'Shamrock' variety (non-patented in the United States).

Plant:

*Type.*—Hardy evergreen shrub for garden decoration and general landscape use.

*Growth habit.*—Compact, with a slightly wide oval upright growth habit. The overall growth habit is smaller than that of the 'Shamrock' parent.

*Height.*—Approximately 20 to 30 inches at an age of five years.

*Width.*—Approximately 15 to 22 inches at an age of five years.

Leaves:

*Shape.*—Narrowly obovate to oblanceolate to narrowly elliptic.

*Blade length.*—Approximately 1.5 to 3.4 cm.

*Blade width.*—Approximately 0.7 to 1.25 cm.

*Petiole.*—Approximately 0.3 to 0.5 cm in length.

*Margins.*—Mostly entire and commonly with a few serrulate teeth near the apex. Rarely are the leaves completely entire.

*Apex.*—Obtuse to broadly obtuse to broadly acute. Occasionally a murconate tip is present.

*Base.*—Narrowly cuneate.

*Texture.*—Glabrous and glossy.

*Arrangement.*—Alternate.

*Venation.*—Pinnately veined with a prominent midrib.

*Color.*—Mature Foliage in the Sun: Upper Surface (Ventral Surface): The central area of the leaf blade is composed of irregular elongated areas that are predominantly near and through Green Group 131A, Green Group 136A, Green Group 139A, and near Yellow-Green Group 144A. The irregular variegation of the margins is near and through Yellow Group 13A, Yellow Group 13B, Yellow-Orange Group 14A, and Yellow-Orange Group 15B. As the season progresses, some of the variegated areas may shift towards Yellow-Green Group 151A and near Yellow-Green Group 153A. Infrequently shoots bearing mature leaves that are completely of the golden yellow coloration commonly displayed on leaf margins have been observed. Such infrequent shoot coloration when present commonly has been observed not to persist much beyond the season in which it was initially produced. Under Surface (Dorsal Surface): The irregular central area is near Yellow-Green Group 147B and Green Group 137C. The irregular margins commonly are near Yellow-Green Group 151A. Mature Foliage in the Shade: Upper Surface (Ventral Surface): The central area of the leaf blade is predominantly composed of irregular elongated areas that are predominantly near and through Green Group 137A, Green Group 137B, Green Group 139A, Yellow-Green Group 141A, and Yellow-Green Group 141B. The margins commonly are near Yellow-Green Group 144A. Under Surface (Dorsal Surface): The central area of the leaf blade is predominantly near Green Group 137C. The margin is near Yellow-Green Group 144A.

Inflorescence:

*Type.*—Forms dioecious female flowers usually solitary on a slender short stalk.

*Bearing.*—In leaf axils of current season growth.

*Time.*—Usually mid- to late-May to early-June.

*Color.*—White, near White Group 155A.

*Petal number.*—Commonly 5 to 8.

*Petal shape.*—Obovate.

*Pistil.*—One per flower.

*Fragrance.*—None observed.

*Fruit.*—None observed; however, plants to date have been grown in absence of a male pollen source.

Disease resistance: No susceptibility or resistance to common Ilex diseases or pests has been observed to date under commercial growing conditions and when grown in unsprayed areas.

The new 'Gold Mine' variety has not been observed under all possible environmental conditions to date. Thus, it possible that some variation in phenotypic expression may be displayed under different light intensity and duration and different cultural conditions.

I claim:

1. A new and distinct *Ilex glabra* plant that displays the following combination of characteristics:

(a) when exposed to full sun the foliage is dark glossy green with irregular bright golden yellow variegation at the margin, (b) exhibits a slow to moderate growth habit, (c) forms dioecious female flowers, (d) assumes a smaller overall size than the parent 'Shamrock' variety (non-patented in the United States), and (e) displays good hardiness in U.S.D.A. Hardiness Zone No. 6a;

substantially as illustrated and described.

* * * * *

*Ilex glabra* 'Gold Mine'
0 1cm 2 3 4 5 6 7 8 9 1

*Ilex glabra* 'Gold Mine'
0 1cm 2 3 4 5 6 7 8 9 10 11

Ilex glabra 'Gold Mine'
1 2 3 4 5 6 7 8 9 10 11

*Ilex glabra* 'Gold Mine'
0 1 2 3 4 5 6 7 8 9 10 11